United States Patent
Mikami et al.

(10) Patent No.: US 7,148,042 B2
(45) Date of Patent: Dec. 12, 2006

(54) METHOD OF PREPARING A GUANOSINE-GROUP COMPOUND AND AN INTERMEDIATE THEREOF

(75) Inventors: Yoichi Mikami, Tokyo (JP); Seiichiro Matsumoto, Tokyo (JP); Yoshinori Hayashi, Tokyo (JP); Toyoki Sato, Tokyo (JP)

(73) Assignee: Yuki Gosei Kogyo Co., Ltd., Tokyo (JP)

( * ) Notice: Subject to any disclaimer, the term of this patent is extended or adjusted under 35 U.S.C. 154(b) by 539 days.

(21) Appl. No.: 10/615,265

(22) Filed: Jul. 8, 2003

(65) Prior Publication Data

US 2004/0072303 A1    Apr. 15, 2004

Related U.S. Application Data

(62) Division of application No. 09/808,448, filed on Mar. 14, 2001, now Pat. No. 6,620,596.

(30) Foreign Application Priority Data

Mar. 27, 2000    (JP) ............................. 2000-087302

(51) Int. Cl.
    *C12P 19/40*    (2006.01)
(52) U.S. Cl. ..................... 435/88; 435/193; 435/252.5; 435/87; 435/89; 536/124; 536/27.1; 536/27.3

(58) Field of Classification Search .................... None
    See application file for complete search history.

(56) References Cited

FOREIGN PATENT DOCUMENTS

| EP | 0 411 158 A1 | 2/1990 |
|---|---|---|
| EP | 0 896 065 A1 | 2/1999 |
| JP | 05 170 767 | * 7/1993 |

OTHER PUBLICATIONS

Palladino et al., J. Am. chem. Soc., 1986 108(19), 6066-6068.*
Chemical Abstracts Service, Columbus, Ohio, US, XP-002191262, abstract of Chung et al., *Carcinogenesis* 6(11), 1671-3 (1985).
Paladino et al., *J. Am. chem., Soc.*, 1986 108(19), 6066-6068.

* cited by examiner

*Primary Examiner*—Irene Marx
(74) *Attorney, Agent, or Firm*—Jones Day

(57) ABSTRACT

A glyoxal-guanosine-group compound is prepared either by reacting glyoxal-guanine with any one of ribose-1-phosphate and 2-deoxyribose-1-phosphate in the presence of purine nucleoside phosphorylase, or by reacting glyoxal-guanine with any one selected from the group consisting of uridine, 2'-deoxyuridine and thymidine, together with phosphate ion, in the presence of purine nucleoside phosphorylase and pyrimidine nucleoside phosphorylase. The glyoxal-guanosine-group compound is then decomposed by alkali, whereby a guanosine-group compound consisting of guanosine and 2'-deoxyguanosine is prepared.

8 Claims, No Drawings

METHOD OF PREPARING A GUANOSINE-GROUP COMPOUND AND AN INTERMEDIATE THEREOF

CROSS-REFERENCE TO RELATED APPLICATIONS

This application is a divisional of U.S. patent application Ser. No. 09/808,448, filed Mar. 14, 2001, now U.S. Pat No. 6,620,596, which is based upon and claims the benefit of priority from the prior Japanese Patent Application No. 2000-087302, filed Mar. 27, 2000, the entire contents of which are incorporated herein by reference.

BACKGROUND OF THE INVENTION

The present invention relates to a method of preparing a guanosine-group compound, which is used as a raw material of an anti-virus agent, antisense medicine and the like, and a method of preparing a glyoxal-guanosine-group compound as an intermediate of the guanosine-group compound.

Guanosine or 2'-deoxyguanosine is industrially produced mainly by extraction/separation of hydrolysate of DNA (deoxyribonucleic acid) or RNA (ribonucleic acid), because the yield is extremely low when guanosine or 2'-deoxyguanosine is chemically synthesized. However, the hydrolysate of DNA contains 2'-deoxyadenosine, 2'-deoxycytidine and thymidine other than the targeted 2'-deoxyguanosine. The hydrolysate of RNA contains adenosine, cytidine and uridine other than the targeted guanosine. Accordingly, in order to collect only guanosine or 2'-deoxyguanosine, it is necessary to perform complicated processes of extraction/separation, thereby inevitably raising the production cost.

On the other hand, a method has been reported in which nucleoside (or deoxynucleoside) and nucleic acid base, which are the raw materials, are subjected to a base-exchange reaction by nucleoside phosphorylase, whereby the aimed nucleoside (or the aimed deoxynucleoside) is obtained (Hori, N., Watanabe, M., Yamazaki, Y., Mikami, Y., Agric. Biol. Chem., 53, 197–202 (1989)). By this method, adenosine and 2'-deoxyadenosine can be easily prepared (Jpn. Pat. Appin. KOKAI Publication No. 11-46790 "Method of preparing a purine nucleoside compound"). In order to obtain guanosine and 2'-deoxyguanosine by this method of enzymatic synthesis reaction, guanine must be soluble to water at least in a range of pH where the enzymes necessary for the reaction can function. In general, it is considered that the solubility of the reaction substrate is preferably at least equal to the concentration of Michaelis constant (Km) of the enzyme or higher, in order to carry out the enzyme reaction smoothly. However, as the solubility of guanine to water does not exceed a few ppm the above method of enzymatic synthesis reaction cannot be employed in practice. Due to such an impasse-like situation, it has been demanded to develop a method of efficiently preparing guanosine or 2'-deoxyguanosine.

BRIEF SUMMARY OF THE INVENTION

An object of the present invention is to provide a method of efficiently preparing guanosine or 2'-deoxyguanosine (i.e., a guanosine-group compound) at a high yield, as well as a method of efficiently preparing a glyoxal-guanosine or glyoxal-2'-deoxyguanosine (i.e., glyoxal-guanosine-group compound) as an intermediate of the guanosine-group compound at a high yield.

The inventors of the present invention have assiduously studied for solving the aforementioned problems. As a result, the inventors have discovered the following 1)–6):

1. When guanine, whose solubility to water does not exceed a few ppm, is reacted with glyoxal, glyoxal-guanine represented by the following formula (1) is obtained, and glyoxal-guanine is soluble to water.

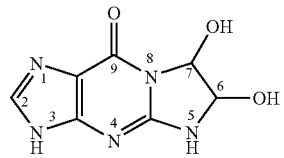

(1)

(Glyoxal-guanine is also referred to as 6,7-dihydro-6,7-dihydroxyimidazo[1,2-a]purine-9(3H)-one.)

2. When microorganism itself which contains purine nucleoside phosphorylase (EC 2.4.2.1) or this enzyme derived from the microorganism are applied, for a reaction, to glyoxal-guanine and any one of ribose-1-phosphate and 2-deoxyribose-1-phosphate, a glyoxal-guanosine-group compound (i.e., glyoxal-guanosine or glyoxal-2'-deoxyguanosine) represented by the following formula (2) is obtained. Alternatively, when microorganism itself which contains purine nucleoside phosphorylase (EC 2.4.2.1) and pyrimidine nucleoside phosphorylase (EC 2.4.2.2) or these enzymes derived from the microorganism are applied, for a reaction, to glyoxal-guanine and any one selected from the group consisting of uridine, 2'-deoxyuridine and thymidine under the presence of phosphate ion, a glyoxal-guanosine-group compound (i.e., glyoxal-guanosine or glyoxal-2'-deoxyguanosine) represented by the following formula (2) is obtained. In other words, glyoxal-guanine can be a substrate of purine nucleoside phosphorylase.

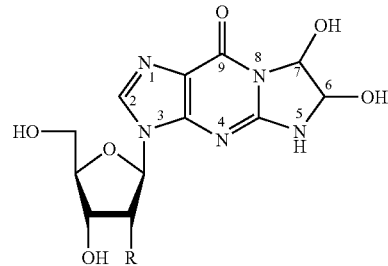

(2)

(wherein R represents a hydrogen atom or a hydroxyl group.)

(Glyoxal-guanosine is also referred to as 3-(β-D-erythro-pentofuranosyl)-6,7-dihydro-6,7-dihydroxyimidazo[1,2-a]purine-9(3H)-one, and g:Lyoxal-2'-deoxyguanosine is also referred to as 3-(2-deoxy-β-D-erythropentofuranosyl)-6,7-dihydro-6,7-d:ihydroxyimidazo[1,2-a]purine-9(3H)-one.)

3. In the method of preparing a glyoxal-guanosine-group compound described in 2) above, when at least one compound selected from the group consisting of glycine, iminodiacetic acid, nitrilotriacetic acid, ethylenediaminetetraacetic acid (which will be referred to as "EDTA" hereinafter), ethylene glycol bis(β-aminoethyl ether)-N,N, N', N'-tetraacetic acid (which will be referred to as "EGTA" hereinafter) and salts of these substances is added, or the above at least one compound is added in combination with boric acid or a salt thereof, the reaction yield is significantly improved. The above compound is added as a stabilizer of ribose-1-phosphate or 2-deoxyribose-1-phosphate, which is the substrate or an intermediate produced during base-exchange reaction.

4. As a principle, nucleoside phosphorylase derived from various organism can be efficient as the enzyme to be used in the preparation method of 2) above. However, the enzyme derived from microorganism of *Bacillus* genus, *Escherichia* genus or *Klebsiella* genus is suitable, and the thermotolerant enzyme derived from *Bacillus stearothermophilus* JTS 859 (FERM BP-6885) is especially preferable.

5. When an alkali is applied, for a reaction, to the glyoxal-guanosine-group compound obtained by the method of 2) above, the glyoxal portion of the glyoxal-guanosine-group compound is easily released, whereby a guanosine-group compound (i.e., guanosine or 2'-deoxyguanosine) can be obtained.

6. The preparation processes of the aforementioned 1)–5) can be carried out by one-pot reaction.

On the basis of the aforementioned discoveries, the present invention has been completed.

In summary, the present invention relates to the following methods (1)–(16):

(1) A method of preparing a glyoxal-guanosine-group compound represented by formula (2):

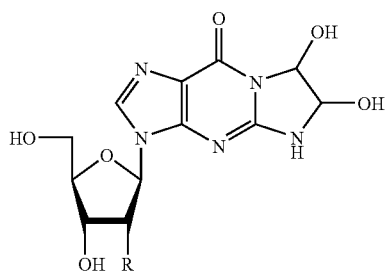

(2)

wherein R represents a hydrogen atom or a hydroxyl group, which comprises the step of:
reacting glyoxal-guanine represented by formula (1):

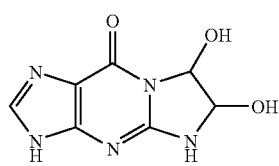

(1)

with ribose-1-phosphate or 2-deoxyribose-1-phosphate in the presence of purine nucleoside phosphorylase, thereby obtaining a glyoxal-guanosine or glyoxal-2'-deoxyguanosine.

(2) A method of preparing a glyoxal-guanosine-group compound represented by formula (2):

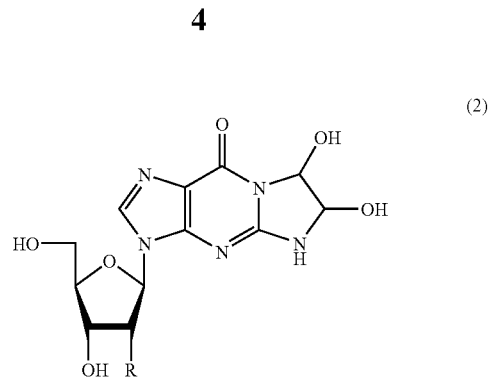

(2)

wherein R represents a hydrogen atom or a hydroxyl group, which comprises the step of:
reacting glyoxal-guanine represented by formula (1):

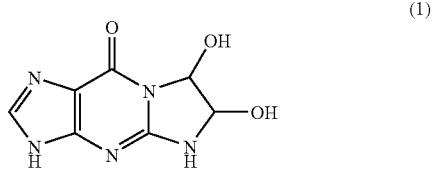

(1)

with any one selected from the group consisting of uridine, 2'-deoxyuridine and thymidine, together with phosphate ion, in the presence of purine nucleoside phosphorylase and pyrimidine nucleoside phosphorylase, thereby obtaining a glyoxal-guanosine or glyoxal-2'-deoxyguanosine.

(3) A method of preparing a guanosine-group compound, which comprises the steps of:
reacting glyoxal-guanine represented by formula (1):

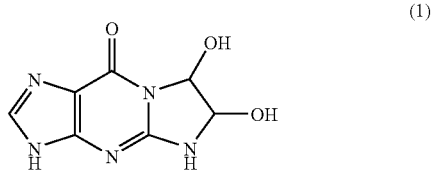

(1)

with ribose-1-phosphate or 2-deoxyribose-1-phosphate in the presence of purine nucleoside phosphorylase, thereby obtaining a compound represented by formula (2):

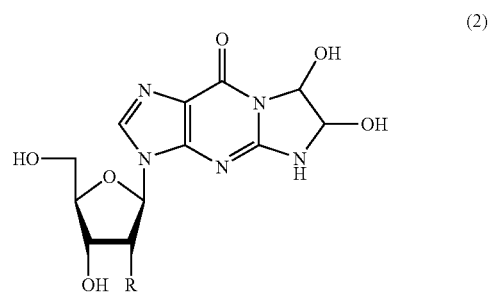

(2)

wherein R represents a hydrogen atom or a hydroxyl group; and decomposing, by alkali, the compound represented by formula (2), thereby obtaining guanosine or 2'-deoxyguanosine.

(4) A method of preparing a guanosine-group compound, which comprises the steps of:

reacting glyoxal-guanine represented by formula (1):

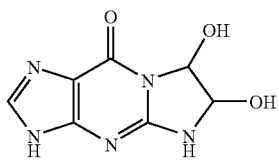

(1)

with any one selected from the group consisting of uridine, 2'-deoxyuridine and thymidine, together with phosphate ion, in the presence of purine nucleoside phosphorylase and pyrimidine nucleoside phosphorylase, thereby obtaining a compound represented by formula (2):

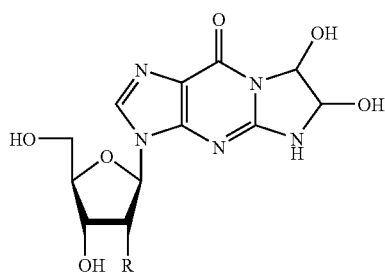

(2)

wherein R represents a hydrogen atom or a hydroxyl group; and decomposing, by alkali, the compound represented by formula (2), thereby obtaining guanosine or 2'-deoxyguanosine.

(5) A method of preparing a glyoxal-guanosine-group compound described in the aforementioned (1), wherein, as purine nucleoside phosphorylase, a microorganism itself which contains the enzyme or the enzyme derived from the microorganism is used.

(6) A method of preparing a glyoxal-guanosine-group compound described in the aforementioned (2), wherein, as purine nucleoside phosphorylase and pyrimidine nucleoside phosphorylase, a microorganism itself which contains the enzymes or the enzymes derived from the microorganism are used.

(7) A method of preparing a guanosine-group compound described in the aforementioned (3), wherein, as purine nucleoside phosphorylase, a microorganism itself which contains the enzyme or the enzyme derived from the microorganism are used.

(8) A method of preparing a guanosine-group compound described in the aforementioned (4), wherein, as purine nucleoside phosphorylase and pyrimidine nucleoside phosphorylase, a microorganism itself which contains the enzymes or the enzymes derived from the microorganism are used.

(9) A method of preparing a glyoxal-guanosine-group compound described in the aforementioned (5) or (6), wherein the microorganism belongs to *Bacillus* genus, *Escherichia* genus or *Klebsiella* genus.

(10) A method of preparing a guanosine-group compound described in the aforementioned (7) or (8), wherein the microorganism belongs to *Bacillus* genus, *Escherichia* genus or *Klebsiella* genus.

(11) A method of preparing a glyoxal-guanosine-group compound described in any one of the aforementioned (5), (6) and (9), wherein the microorganism is *Bacillus stearothermophilus* JTS 859 (FERM BP-6885), *Escherichia coli* IFO 3301, *Escherichia coli* IFO 13168, or *Klebsiella pneumoniae* IFO 3321.

(12) A method of preparing a guanosine-group compound described in any one of the aforementioned (7), (8) and (10), wherein the microorganism is *Bacillus stearothermophilus* JTS 859 (FERM BP-6885), *Escherichia coli* IFO 3301, *Escherichia coli* IFO 13168, or *Klebsiella pneumoniae* IFO 3321.

(13) A method of preparing a glyoxal-guanosine-group compound described in any one of the aforementioned (1), (2), (5), (6), (9) and (11), wherein at least one compound selected from the group consisting of glycine, iminodiacetic acid, nitrilotriacetic acid, ethylenediaminetetraacetic acid, ethylene glycol bis(β-aminoethyl ether)-N,N,N',N'-tetraacetic acid and salts thereof is added, or the above at least one compound is added in combination with boric acid or a salt thereof

(14) A method of preparing a guanosine-group compound described in any one of the aforementioned (3), (4), (7), (8), (10) and (12), wherein at least one compound selected from the group consisting of glycine, iminodiacetic acid, nitrilotriacetic acid, ethylenediaminetetraacetic acid, ethylene glycol bis(β-aminoethyl ether)-N,N,N', N'-tetraacetic acid and salts thereof is added, or the above at least one compound is added in combination with boric acid or a salt thereof.

(15) A method of preparing a glyoxal-guanosine-group compound described in any one of the aforementioned (1), (2), (5), (6), (9), (11) and (13), which is performed by one-pot reaction.

(16) A method of preparing a guanosine-group compound described in any one of the aforementioned (3), (4), (7), (8), (10), (12) and (14), which is performed by one-pot reaction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The present invention will be described in detail hereinafter.

Raw Material

Glyoxal-guanine (i.e., 6,7-dihydro-6,7-dihydroxyimidazo[1,2-a]purine-9(3H)-one) to be used as a raw material in the present invention can be prepared at a high yield by adding guanine to a glyoxal aqueous solution and stirring the mixture with heating at a high temperature (preferably at 50–75° C.) for about 15–20 hours. The solubility of glyoxal-guanine to water increases as the temperature rises. After the completion of the reaction, glyoxal-guanine is crystallized by cooling and can be obtained as a white solid by filtering.

However, when one-pot reaction is carried out by continuously adding nucleoside phosphorylase and either ribose donor or 2-deoxyribose donor, the solution in which glyoxal-guanine has been obtained may be used, as it is, as a raw material solution.

In the present invention, ribose-1-phosphate and uridine used as the ribose donor, and 2-deoxyribose-1-phosphate, 2'-deoxyuridine and thymidine used as the 2-deoxyribose donor are commercially available by, for example, Sigma Aldrich Japan Co.

Synthesis Conditions of a Glyoxal-Guanosine-Group Compound by the Enzyme Reaction The ribose donor or the 2-deoxyribose donor (which will be referred to as "the ribose-group donor" hereinafter) and glyoxal-guanine are added to a phosphate buffer solution (pH 6–8, preferably pH 7). Microorganism itself or the enzymes derived from the microorganism, which produces purine nucleoside phosphorylase and pyrimidine nucleoside phosphorylase (or only purine nucleoside phosphorylase), is added to the above phosphate buffer mixture. The resultant reaction mixture is stirred at the optimum temperature for the enzyme for 24–60 hours, resulting in reactions as represented by "Reaction formula 1 and Reaction formula 2" or "Reaction formula 3 and Reaction formula 4". Glyoxal-2'-deoxyguanosine is obtained by "Reaction formula 1 and Reaction formula 2". Glyoxal-guanosine is obtained by "Reaction formula 3 and Reaction formula 4". In Reaction formula 1 and Reaction formula 3 as the former half part, pyrimidine nucleoside phosphorylase is used as the enzyme in the reaction. In Reaction formula 2 and Reaction formula 4 as the latter half part, purine nucleoside phosphorylase is used as the enzyme in the reaction. With respect to the optimum temperature for the enzyme, the temperature may be in the range of approximately 40–70° C. in the case of the enzyme derived from *Bacillus stearothermophilus* JTS 859 (FERM BP-6885).

In the enzyme reaction of the present invention, purine nucleoside phosphorylase and pyrimidine nucleoside phosphorylase (or only purine nucleoside phosphorylase) are used. When pyrimidine nucleoside (uridine, 2'-deoxyuridine, or thymidine) is used as the ribose-group donor, pyrimidine nucleoside phosphorylase is essentially required for producing ribose-1-phosphate or 2-deoxyribose-1-phosphate in "Reaction formula 1" or "Reaction formula 3" as the former half reaction. On the other hand, when ribose-1-phosphate or 2-deoxyribose-1-phosphate is used as the ribose-group donor from the start of the reaction, the reaction represented by "Reaction formula 1" or "Reaction formula 3" is not necessitated, and thus pyrimidine nucleoside phosphorylase is not required. However, in this case, even if pyrimidine nucleoside phosphorylase is present, the overall enzyme reaction will not be adversely affected at all.

In Reaction formulae 1–4, "PYNP" represents pyrimidine nucloside phosphorylase, and "PUNP" represents purine nucleoside phosphorylase.

(Reaction formula 1):

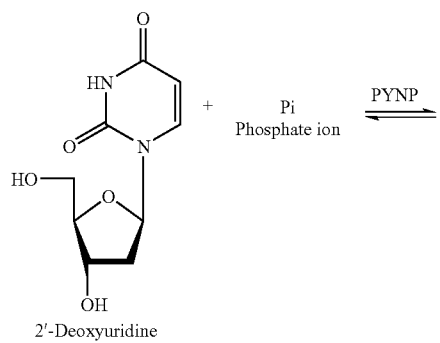

2'-Deoxyuridine

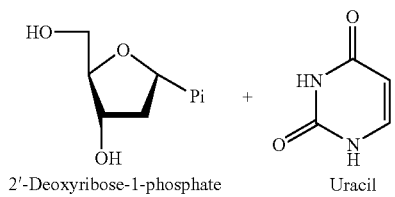

2'-Deoxyribose-1-phosphate   Uracil (Reaction formula 2):

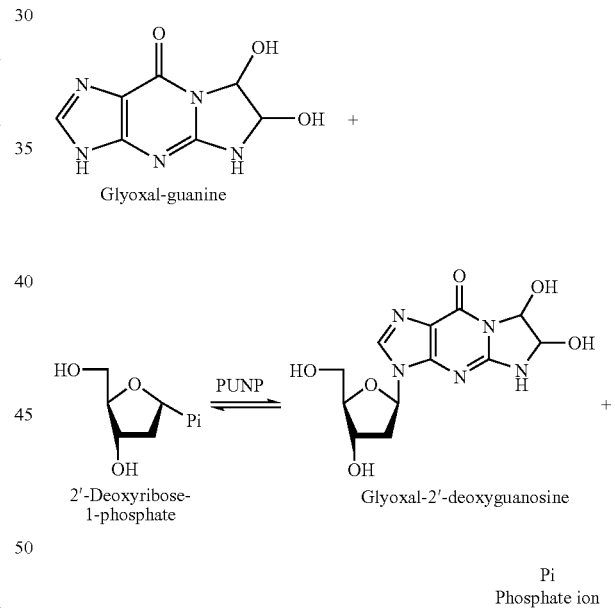

Glyoxal-guanine

2'-Deoxyribose-1-phosphate    Glyoxal-2'-deoxyguanosine

Pi
Phosphate ion (Reaction formula 3):

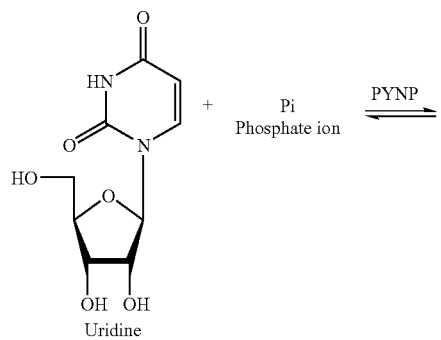

Uridine

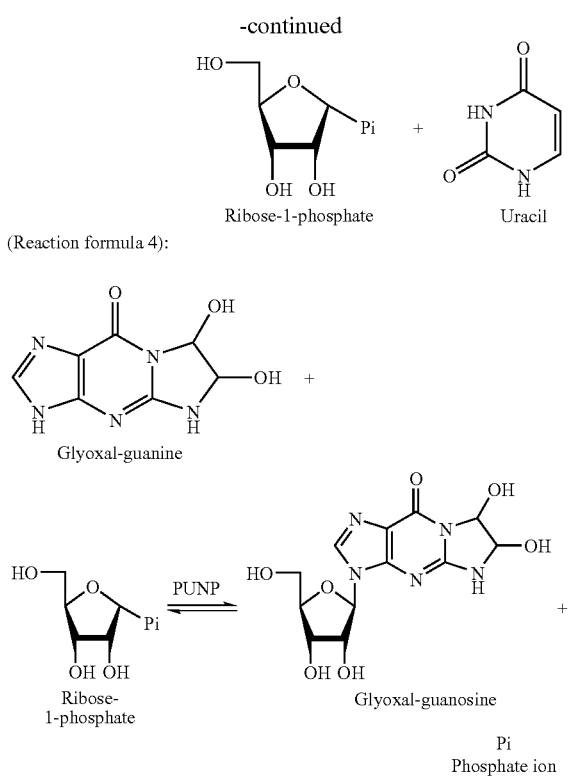

(Reaction formula 4):

In the present invention, the initial concentration of the ribose-group donor as the raw material is 5–1000 mM, preferably 10–100 mM. Glyoxal-guanine does not dissolve in a large amount at a time. However, if it is assumed that the initially added amount of glyoxal-guanine were to be completely dissolved at a time, the expressed initial concentration would be 5–1000 mM, preferably 10–100 mM. The initial concentration of phosphate ion of 1–20 mM suffices the purpose.

Stabilizer of deoxyribose-1-phosphate, etc.

In the present invention, even when a nucleoside (uridine, 2'-deoxyuridine, thymidine) is used as the raw material, the reaction proceeds by way of ribose-1-phosphate or 2-deoxyribose-1-phosphate as the reaction intermediate, as shown in the aforementioned formulae. These phosphate compounds are unstable by nature and, when being left, naturally decomposed into ribose and phosphate ion or 2-deoxyribose and phosphate ion as time passes. When phosphatase is present in the reaction system, the decomposition is accelerated. If such decomposition occurs, the production efficiency of glyoxal-guanosine group compound is decreased, because ribose or 2-deoxyribose, which is the product by decomposition of the intermediate, does not serve as the substrate of nucleoside phosphorylase. Therefore, in order to increase the production efficiency, a substance, which stabilizes ribose-1-phosphate or 2-deoxyribose-1-phosphate and inhibits the activity of phosphatase, has been searched in the present invention.

As a result, it has been discovered that addition of at least one compound selected from the group consisting of glycine, iminodiacetic acid, nitrilotriacetic acid, EDTA, EGTA and salts thereof, and more preferably, addition of the above at least one compound in combination with boric acid or a salt thereof is effective. The combination of EDTA or a salt thereof with boric acid or a salt thereof exhibits a signifi-cantly excellent effect. The preferable concentration of each composition added is 20–200 mM for boric acid or a salt thereof, and 2–10 mM for the above at least one compound or salts thereof (i.e., glycine, iminodiacetic acid, nitrilotriacetic acid, EDTA, EGTA). Salts of the above compounds and a salt of boric acid used herein are not particularly limited, and any salts can be used. For example, the salts used herein may be salts of alkaline metal such as sodium and potassium, or salts of alkaline earth metal such as calcium and magnesium.

Preparation of a Guanosine-Group Compound from a Glyoxal-Guanosine-Group Compound A glyoxal-guanosine-group compound releases, by decomposition, the glyoxal portion thereof in an alkali aqueous solution, thereby obtaining a guanosine-group compound. As the alkali aqueous solution, 0.05–0.5N, preferably 0.1–0.25N sodium hydroxide aqueous solution can be used, for example. This decomposition reaction is accelerated by the increase in pH and temperature. However, it is essential to select a mild condition in which the bonding with ribose-group is not broken. Specifically, a glyoxal-guanosine-group compound is relatively stable in the range of pH 4–8, but is decomposed and releases the glyoxal portion thereof at pH 9 or higher. In conclusion, it is preferable that a glyoxal-guanosine-group compound is decomposed at 60–80° C. in the range of pH 9–11 in 1–5 hours duration, to obtain a guanosine-group compound.

Separation and Purification of a Guanosine-group Compound

Collection of the product from the reaction solution can be performed by ultrafiltration, ion exchange separation, adsorption chromatography, crystallization and the like. The amount of the reaction product can be determined by the HPLC method using a UV detector.

Microorganism and Enzyme

Purine nucleoside phosphorylase (EC 2.4.2.1) and pyrimidine nucleoside phosphorylase (EC 2.4.2.2) used in the present invention may have any origin as a principle. The enzymes produced by the microorganism described below are preferable. The microorganism to be used in the present invention is not particularly limited to such examples, as long as the microorganism produces the aforementioned enzymes in a significant amount.

However, as shown in the aforementioned Reaction formulae, the present reactions employ nucleoside or 2'-deoxynucleoside as the substrate and thus inevitably produce a phosphate compound as the intermediate. Accordingly, microorganism which shows a strong nucleosidase and/or phosphatase activity cannot be utilized.

Examples of the microorganism which suffices these conditions include those which belong to *Bacillus* genus, *Escherichia* genus or *Klebsiella* genus. More specifically, the examples include *Bacillus stearothermophilus* JTS 859 (FERM BP-6885), *Escherichia coli* IFO 3301, *Escherichia coli* IFO 13168, and *Klebsiella pneumoniae* IFO 3321.

In the present reaction, the higher the solubility and the dissolving rate of the raw material are, the higher yield and the higher reaction rate are obtained. Accordingly, a relatively high temperature during the reaction is advantageous. Due to this, use of thermophilic bacteria and heat-resistant enzymes is preferable. Among the aforementioned examples of microorganisms, *Bacillus stearothermophilus* JTS 859 is the most preferable.

"IFO" indicates that the microorganisms are preserved in Institute for Fermentation, Osaka (IFO), Feb. 17, 1985, Zyusohonmachi, Yodogawa-ku, Osaka-shi, 532-0024 JAPAN. The "IFO strains" are available to any person, if desired. *Bacillus stearothermophilus* JTS 859 is under international deposit (the deposit number thereof is FERM BP-6885) in Patent Microorganism Depository, National Institute of Bioscience and Human-Technology, Agency of Industrial Science and Technology. The microorganism *Bacillus stearothermophilus* JTS 859 (FERM BP-6885) was deposited as a national deposit, on Oct. 20, 1987, in the National Institute of Bioscience and Human-Technology, Agency of Industrial Science and Technology, Japan (1-3, Higashi 1-Chome, Tsukubashi, Ibaraki-ken, Japan), which is an international deposit authority designated by the BUDAPEST TREATY ON THE INTERNATIONAL RECOGNITION OF THE DEPOSIT OF MICROORGANISMS FOR THE PURPOSES OF PATENT PROCEDURE. National deposit number P-9666 was assigned to the strain JTS 859. Thereafter, the strain JTS 859 was transferred from the national deposit to an international deposit on Sep. 22, 1999, and international deposit number FERM BP-6885 was assigned to it.

These types of microorganisms are grown on the normal culture medium for bacteria, and show better growth and produce a larger amount of the aforementioned enzyme by adding tryptone, yeast extract, glucose and the like. Further, addition of a nucleic acid compound such as inosine to the culture medium is effective in enhancing the activity of the enzyme. The cultured bacteria itself may be utilized as the crude enzyme. Alternatively, enzyme is obtained from the cultured bacteria by the standard methods (such as destruction by supersonication or milling, centrifugation, ammonium sulfate-fractionation, and membrane separation), and the resultant crude enzyme may also be employed.

The results of studying the bacteriological characteristics of the deposited strain according to "Bergey's Manual of Determinative Bacteriology, Volume II" (1984) are as follows. The experiments were basically carried out by the method described in "Biseibutsu no Bunrui to Dotei (Classification and Determination of Microorganism)" by Takeji Hasegawa, edited version, Gakkai Shuppan center, 1985.

*Bacillus stearothermophilus* JTS 859 (FERM BP-6885):

1. Morphological characteristics (1) Shape and size of the cell: Rod, 5.4–6.5 μm×0.7–0.9 μm (2) Spore: Ellipsoidal-shaped spore is formed. One spore in one cell, the spore being positioned at the end of the cell.

2. Characteristics in culture (1) Bouillon liquid culture: culture at 62° C. for 2 days.

(2) Bouillon agar plate culture: White with slightly yellow tint, glossy, opaque, not piling up. The colony has a wavy circular shape.

(3) Bouillon agar slant culture: White with slightly yellow tint, glossy, opaque, not piling up. Moderate growth.

3. Biochemical characteristics

| (1) | Gram's stain | positive |
|---|---|---|
| (2) | Anaerobic culture | no growth |
| (3) | Motility | peritrichous movement |
| (4) | Oxidase | positive |
| (5) | Catalase | positive |
| (6) | Liquefiability of gelatin | liquefiable |
| (7) | Litmus milk | coagulated |
| (8) | O-F Test | fermentation type |
| (9) | VP Test | negative |

-continued

| (10) | Gas generation from D-gluxcose | no generation |
|---|---|---|
| (11) | Production of Acid from D-glucose | produced |
| (12) | Production of Acid from L-arabinose | not produced |
| (13) | Production of Acid from D-mannitol | produced |
| (14) | Production of Acid from D-oxylose | not produced |
| (15) | Growth in Sabouraud's medium | |
| | Slant | Growth was observed |
| | Liquid | Growth was observed |
| (16) | Growth under 0.001% lysozyme | no growth |
| (17) | Growth under 0.02% azide | no growth |
| (18) | Growth under 7% NaCl | no growth (grew up to 2% level) |
| (19) | Hydrolysis of casein | hydrolyzable |
| (20) | Hydrolysis of starch | hydrolyzable |
| (21) | Egg-yolk Test | no growth |
| (22) | Production of dihydroxyacetone | not produced |
| (23) | Utilization of citric acid | negative |
| (24) | Production of indole | negative |
| (25) | Activity of urease | positive |
| (26) | Deamination of phenylalanine | negative |
| (27) | Activity of arginine dihydrolase | positive |
| (28) | Decomposition of tyrosine | negative |
| (29) | Production of levan | negative |
| (30) | Reduction of a nitrate | positive |
| (31) | Denitrification of sodium nitrate | negative |
| (32) | Production of hydrogen sulfide | Positive |
| (33) | Utilization of inorganic nitrogen source | |
| | with $NO_3$ as the only nitrogen source | Growth was observed |
| | with $NH_4$ as the only nitrogen source | Growth was observed |
| (34) | GC content | 47.3% |
| (35) | Growth temperature | |
| | Range | 40–71° C. |
| | Optimum Range | 60–68° C. |
| (36) | Growth pH | |
| | Range | 5.7–8.5 |
| | Optimum Range | 6.0–7.0 |

Judging from the aforementioned characteristics, the present strain can be determined to be *Bacillus stearothermophilus*.

One-Pot Reaction

The method of preparing a glyoxal-guanosine-group compound and the method of preparing a guanosine-group compound of the present invention can be both carried out by a one-pot reaction. Specifically, the initial reaction solution is first prepared by reacting guanosine with a glyoxal aqueous solution. The ribose-group donor (preferably together with a stabilizer), the enzyme solution required for the reaction, and optionally the phosphate ion are added, for the reaction, to the initial reaction solution, whereby a glyoxal-guanosine-group compound can be prepared by a one-pot reaction. In addition, by alkali-decomposing the reaction product, a guanosine-group compound can be prepared by a one-pot reaction.

EXAMPLES

The present invention will further be described in detail by following Production Examples, Experiment Example, and Examples.

Production Example 1

Synthesis of Glyoxal-guanine 22.65 g of guanine (manufactured by Tokyo Kasei Kogyo Co.) and 21.75 g of a 40% glyoxal aqueous solution (manufactured by Tokyo Kasei Kogyo Co.) were added to 950 mL of purified water, and the mixture was stirred with heating at 70° C. for 18 hours. The mixture was then cooled to 4° C.

and filtered. The white solid obtained by the filtration was dried, thereby resulting in 30.7 g of glyoxal-guanine. The measurement result of nuclear magnetic resonance (NMR) spectrum is as follows:

1H-NMR (DMSO-d6, 200 MHz) δ8.52 (bs, 1H), 7.70 (bs, 1H), 7.16 (d, 1H), 6.39 (d, 1H), 5.46 (d, 1H), 4.83 (d, 1H).

Production Example 2

Preparation of Bacteria Suspension which Contain Nucleoside Phosphorylase

*Bacillus stearothermophilus* JTS 859 (FERM BP-6885), which produces purine nucleoside phosphorylase (which will be referred to as "PUNP" hereinafter) and pyrimidine nucleoside phosphorylase (which will be referred to as "PYNP" hereinafter), was cultured in accordance with the following procedure.

In culturing the bacteria, a culture medium of pH 6.2 made of 10 g of bacto-tryptone, 5 g of yeast extract, 3 g of glucose, 3 g of salt, 1 g of inosine and 1 L of water was used. 100 mL of the aforementioned culture medium was charged into a 500 mL Erlenmeyer flask, a platinum loop of the bacteria collected from slant culture was inoculated into the medium in the flask, and the bacteria in the flask were cultured while shaking gyratingly (200 rpm) at 65° C. for 16 hours, thereby resulting in cultured solution. 1.2 L of the same culture medium was charged into a 2 L-culturing-tank, and 60 mL of the cultured solution was inoculated into the medium in the tank. Then, the bacteria in the tank were cultured, while two stirring vanes (the upper vane and the lower vane, each having diameter of 42 mm) were rotated at 650 rpm, for 6 hours at the air flow rate of 1 vvm, at the culture temperature of 65° C. and within the pH range of 6.5–7.0 (stat). After completing the culture, the bacteria were obtained by centrifuging (10,000 G, 4° C., 15 minutes). The bacteria as a whole were suspended in 40 mL of 10 mM potassium phosphate solution (pH 7), whereby enzyme solution containing PUNP and PYNP (which will be referred to as "the enzyme solution" hereinafter) was obtained.

The enzyme activity required for converting 1 μmol of a substrate into a product in one minute is defined as "1U". The enzyme activity of the enzyme solution was measured by the standard method at 60° C. 1 mL of the enzyme solution exhibited the PUNP activity of 66 U and the PYNP activity of 166 U.

Experiment Example 1

Solubility of Guanine and Glyoxal-guanine

An excess amount of each compound was suspended in water, stirred for 1 hour at each temperature and left for a while. The liquid layer was analyzed with HPLC equipped with a UV detector, under the conditions described below. The results are shown in Table 1.

Conditions of the HPLC analysis:
Detector: UV (260 nm)
Column: Superiorex ODS (manufactured by Shiseido)
Eluent: 0.1M ammonium dihydrogenphosphate solution: methanol=97:3 (v/v)
Flow rate: 1 mL/min
Sample: 20 μL

TABLE 1

| Compound | Solubility at each temperature (mg/kg) | | | |
| --- | --- | --- | --- | --- |
| | 30° C. | 40° C. | 50° C. | 60° C. |
| Guanine | 2 or less | 2 or less | 2 | 2 |
| Glyoxal-guanine | 200 | 275 | 330 | 440 |

Example 1

Synthesis of glyoxal-2'-deoxyguanosine by Nucleoside Phosphorylase 5 mm phosphate buffer (pH 7) containing 30 Mm 2'-deoxyuridine, 30 mM glyoxal-guanine, 100 mM boric acid, and 4 mm disodium ethylenediaminetetraacetate was prepared. 1 mL of the enzyme solution obtained in Production Example 2 was added to 99 mL of the above phosphate buffer mixture, so that the total amount of the resultant reaction mixture was 100 mL. The reaction mixture was kept at 50° C. for 48 hours, allowing the reaction to proceed. The mixture was then filtered at 60° C. and cooled to 4° C. The white crystal obtained by the filtration (the yield was 80%) was subjected to spectrometry. The results are as follows. As a result of comparison with the values described in the reference (Chung, F., Hecht, S. S., Carcinogenesis, 6, 1671–1673 (1985)), it was confirmed that the product was glyoxal-2'-deoxyguanosine.

UV (pH 7), λmax (nm) 248, 272 (shoulder)
1H-NMR (DMSO-d6+D20, 200 MHz), δ7.9.5 (s, 1H, 2-H), 6.12 (t,1H, 1'-H), 5.50 (s, 1H, 7-H), 4.90 (s, 1H, 6-H), 4.35 (bs, 1H, 3'-H), 3.83 (bs, 1H, 4'-H), 3.54 (m, 2H, 5'-H), 2.52 (m, 1H, 2'-H), 2.28 (m, 2H, 2'-H).

Example 2

Synthesis of 2'-deoxyguanosine from glyoxal-2'-deoxyguanosine 0.1 g of glyoxal-2'-deoxyguanosine obtained in Example 1 described above was added to 0.2 N sodium hydroxide solution, and stirred at 70° C. for 2 hours. After neutralizing the mixture, an analysis was performed by using the HPLC method, under the conditions of Example 1, thereby confirming that 2'-deoxyguanosine was quantitatively obtained. In addition, the white crystal obtained by chromatography and crystallization was subjected to spectrometry, and it was confirmed from each spectrum that the obtained crystal was 2'-deoxyguanosine.

Example 3

The Effect of the Stabilizer on Amount of glyoxal-2'-deoxyguanosine Formed 5 mM phosphate buffer (pH 7) containing 20 mM 2'-deoxyuridine, 20 mM glyoxal-guanine, the stabilizer shown in Table 2 and 1 mL of the enzyme solution prepared in Production Example 2 was prepared (In Table 2, "*" indicates that the concentration of the stabilizer is 4 mM and the absence of "*" indicates that the concentration of the stabilizer is 100 mM). 100 mL of the above phosphate buffer mixture was kept at 50° C. for 38 hours, allowing the reaction to proceed. Glyoxal-2'-deoxyguanosine contained in the reaction solution was decomposed by alkali, to quantitatively obtain 2'-deoxyguanosine. Then, the concentration of 2'-deoxyguanosine was determined. Further, control solution was prepared in a manner similar to that of preparing the above buffer mixture except for adding 100 mM tris (hydroxymethyl) aminomethane hydrochloric acid ("Tris") instead of the stabilizer. This solution will be referred to as "Tris (control)" hereinafter. From the analysis on the results, it was discovered that the combination of a complex-forming-compound similar to EDTA with boric acid is effective for improving the reaction yield.

TABLE 2

| Stabilizer | Amount of glyoxal-2'-deoxyguanosine formed (mM) |
| --- | --- |
| Tris (control) | 5.4 |
| Boric acid | 4.0 |
| Glycine | 6.0 |
| Iminodiacetic acid * | 8.8 |
| Nitrilotriacetic acid * | 5.4 |
| EDTA * | 9.5 |
| EGTA * | 8.0 |
| Tris and EDTA * | 9.8 |
| Glycine and EDTA * | 10.1 |
| Boric acid and Tris | 5.6 |
| Boric acid and glycine | 6.5 |
| Boric acid and iminodiacetic acid * | 12.4 |
| Boric acid and nitrilotriacetic acid * | 12.2 |
| Boric acid and EDTA * | 12.8 |
| Boric acid and EGTA | 11.5 |

Example 4

Synthesis of glyoxal-2'-deoxyguanosine by the Enzyme Derived from Each Strain 500 mL of the same culture medium as used in Production Example 2 was charged into each of three 2 L Erlenmeyer flasks. *Escherichia coli* IFO 3301, *Escherichia coli* IFO 13168 and *Klebsiella pneumoniae* IFO 3321 was each inoculated into the medium in each of three flasks, by collecting a platinum loop of bacteria each from the stock slant culture. The above bacteria each were cultured while shaking the flasks (200 rpm) at 37° C. for 16 hours, thereby resulting in culture solution. The bacteria were collected by centrifuging (10,000 G, 4° C., 15 minutes) the culture solution. The obtained bacteria was suspended in 10 mL of 10 mM potassium phosphate buffer (pH 7), thereby resulting in three sets of enzyme solutions.

Glyoxal-2'-deoxyguanosine was synthesized from 2'-deoxyuridine and glyoxal-guanine under the following conditions, by using any one of the aforementioned three sets of enzyme solutions and the *Bacillus stearothermophilus* JTS 859 enzyme solution obtained in Production Example 2. Specifically, 5 mM phosphate buffer (pH 7) containing 30 mM 2'-deoxyuridine, 30 mM glyoxal-guanine, 100 mM boric acid, and 4 mM disodium ethylenediaminetetraacetate was first prepared.

Each (2 mL) of the above four sets of enzyme solutions (which contain bacteria corresponding to 100 mL of the above culture solution) was added to 98 mL of the above phosphate buffer mixture, respectively, resulting in four sets of reaction mixtures. Each reaction mixture was kept at each reaction temperature for 48 hours, allowing the reaction to proceed. The results are shown in Table 3.

TABLE 3

| Strain | Reaction temperature (° C.) | Yield of glyoxal-2'-deoxyguanosine (%) |
| --- | --- | --- |
| *Bacillus stearothermophilus* JTS 859 | 50 | 79 |
| *Escherichia coli* IFO 3301 | 30 | 17 |
| *Escherichia coli* IFO 13168 | 30 | 40 |
| *Klebsiella pneumoniae* IFO 3321 | 30 | 23 |

Example 5

Synthesis of a Glyoxal-guanosine-group Compound by Using Various Ribose-group Donor 5 mM phosphate buffer (pH 7) containing each ribose-group donor as shown in Table 4, 20 mM glyoxal-guanine, 100 mM boric acid, and 4 mM disodium ethylenediaminetetraacetate was first prepared (the concentration of each ribose-group donor was 20 mM. However, "*" in Table 4 indicates that the concentration was 10 mM). 0.25 mL of the enzyme solution obtained in Production Example 2 was added to a required amount of the above phosphate buffer mixture, so that the total amount of the resultant reaction mixture was 10 mL. The reaction mixture was kept at 50° C. for 48 hours, allowing the reaction to proceed. The results are shown in Table 4.

TABLE 4

| Ribose-group donor | Nucleoside formed | Yield (%) |
| --- | --- | --- |
| Ribose-1-phosphate * | Glyoxal-guanosine | 78 |
| 2-Deoxyribose-1-phospate * | Glyoxal-2'-deoxyguanosine | 76 |
| Uridine | Glyoxal-guanosine | 61 |
| 2'-Deoxyuridine | Glyoxal-2'-deoxyguanosine | 79 |
| Thymidine | Glyoxal-2'-deoxyguanosine | 63 |

Example 6

Effect of the Substrate Concentration on the Preparation Using the Enzyme Derived from *Bacillus stearothermophilus* JTS 859

5 mM phosphate buffer (pH 7) containing guanine or glyoxal-guanine as the substrate base of each concentration shown in Table 5, 2'-deoxyuridine as the ribose-group donor having the same concentration as each substrate base, 100 mM boric acid, and 4 mM disodium ethylenediaminetetraacetate was first prepared. 1 mL of the enzyme solution obtained in Production Example 2 was added to 99 mL of the above phosphate buffer mixture. The resultant reaction mixture was kept at 50° C. for 48 hours, allowing the reaction to proceed. The results are shown in Table 5. When glyoxal-guanine was selected as the substrate base, the formed glyoxal-2'-deoxyguanosine was decomposed by alkali, to obtain 2'-deoxyguanosine. The amount of the obtained 2'-deoxyguanosine was determined. In Table 5, the analysis was not performed when the concentration of guanine was no less than 50 mM.

TABLE 5

| Concentration of substrate base (mM) | Yield of 2'-deoxyguanosine (%) | | | | | | |
|---|---|---|---|---|---|---|---|
| | 10 mM | 20 mM | 30 mM | 50 mM | 70 mM | 80 mM | 100 mM |
| Guanine (Comparative example) | 29 | 23 | 19 | — | — | — | — |
| Glyoxal-guanine | 81 | 79 | 79 | 77 | 72 | 66 | 64 |

Example 7

Synthesis by One-pot Reaction 0.45 g of guanosine and 0.44 g of a 40% glyoxal aqueous solution were added to 10 mL of water, and the mixture was stirred at 70° C. for 18 hours. Next, the following substances and water were added to the above mixture, thereby resulting in the aqueous solution containing 30 mM 2'-deoxyuridine, 100 mM boric acid, 4 mM disodium ethylenediaminetetraacetate, and 5 mM potassium phosphate, as final concentration. 1 mL of the enzyme solution obtained in Production Example 2 was added to 99 mL of the above aqueous solution, so that the total volume of the resultant reaction mixture was 100 mL. The reaction mixture was kept at 50° C. for 48 hours, allowing the reaction to proceed. Glyoxal-2'-deoxyguanosine contained in the reaction mixture was decomposed by alkali, to 2'-deoxyguanosine. Measurement of the concentration of 2'-deoxyguanosine by HPLC revealed that the yield was 80%.

Example 8

Synthesis of Glyoxal-guanosine 5 mM phosphate buffer (pH 7) containing 50 mM uridine, 50 mM glyoxal-guanine, 100 mM boric acid, and 4 mM disodium ethylenediaminetetraacetate was first prepared. 1 mL of the enzyme solution obtained in Production Example 2 was added to 99 mL of the above phosphate buffer mixture, so that the total volume of the resultant reaction mixture was 100 mL. The reaction mixture was kept at 50° C. for 48 hours, allowing the reaction to proceed. After being filtered with heating, the mixture was cooled to 4° C. The white crystal obtained by the filtration (the yield was 72%) was subjected to spectrometry. The results are as follows. As a result of comparison with spectrum of glyoxal-2'-deoxyguanosine of Example 1, it was confirmed that the product was glyoxal-guanosine.

1H-NMR (DMSO-d6, 200 MHz), δ8.85 (s, 1H, 5-H), 8.00 (s, 1H, 2-H), 7.27 (d, 1H, 7-OH), 6.50 (d, 1H, 6-OH), 5.71 (d,1H, 1'-H), 5.49 (d, 1H, 7-H), 5.44 (d, 1H, 3'-OH), 5.18 (d, 1H, 2'-OH), 5.06 (s, 1H, 5'-OH), 4.88 (d, 1H, 6-H), 4.41 (m, 1H, 2'-H), 4.10 (d, 1H, 3'-H), 3.90 (d, 1H, 4'-H), 3.57 (m, 2H, 5'-H).

Further, guanosine was prepared from the product obtained in this Example, in accordance with the procedure similar to that of Example 2. This fact also revealed that the product obtained in this Example was glyoxal-guanosine.

According to the present invention, a glyoxal-guanosine-group compound can be prepared from the ribose-group donor and the glyoxal-guanine, by the enzyme reactions derived from the microorganism. By alkali decomposing the glyoxal-guanosine-group compound, a guanosine-group compound consisting of guanosine and 2'-deoxyguanosine can be efficiently prepared at a high yield.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of preparing a guanosine-group compound, which comprises the steps of:
   reacting glyoxal-guanine represented by formula (1):

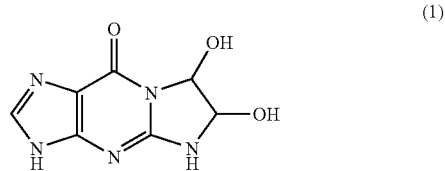

(1)

with ribose-1-phosphate or 2-deoxyribose-1-phosphate in the presence of microbial purine nucleoside phosphorylase, thereby obtaining a compound represented by formula (2):

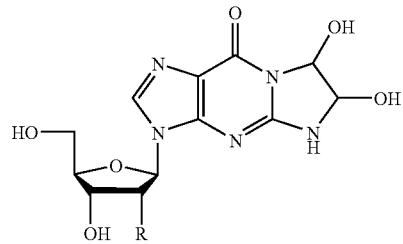

wherein R represents a hydrogen atom or a hydroxyl group; and
   decomposing, by alkali, the compound represented by formula (2), thereby obtaining guanosine or 2'-deoxyguanosine.

2. The method of preparing a guanosine-group compound according to claim 1, wherein the microbial purine nucleoside phosphorylase is contained in a microorganism or is obtained from a microorganism.

3. The method of preparing a guanosine-group compound according to claim 2, wherein the microorganism belongs to *Bacillus* genus, *Escherichia* genus or *Kiebsiella* genus.

4. The method of preparing a guanosine-group compound according to claim 3, wherein the microorganism is *Bacillus stearothermophilus* JTS 859 (FERM BP-6885), *Escherichia coli* IFO 3301, *Escherichia coli* IFO 13168, or *Kiebsiella pneumoniae* IFO 3321.

5. The method of preparing a guanosine-group compound according to claim 1, wherein at least one compound selected from the group consisting of glycine, iminodiacetic acid, nitrilotriacetic acid, ethylenediaminetetraacetic acid, ethylene glycol bis(β-aminoethyl ether)-N,N,N',N'-tetraacetic acid and salts thereof is added, or the above at least one compound is added in combination with boric acid or a salt thereof.

6. The method of preparing a guanosine-group compound according to claim 2, wherein at least one compound selected from the group consisting of glycine, iminodiacetic acid, nitrilotriacetic acid, ethylenediaminetetraacetic acid, ethylene glycol bis(β-aminoethyl ether)-N,N,N',N'-tetraacetic acid and salts thereof is added, or the above at least one compound is added in combination with boric acid or a salt thereof.

7. The method of preparing a guanosine-group compound according to claim 3, wherein at least one compound selected from the group consisting of glycine, iminodiacetic acid, nitrilotriacetic acid, ethylenediaminetetraacetic acid, ethylene glycol bis(β-aminoethyl ether)-N,N,N',N'-tetraacetic acid and salts thereof is added, or the above at least one compound is added in combination with boric acid or a salt thereof.

8. A method of preparing a guanosine-group compound according to claim 4, wherein at least one compound selected from the group consisting of glycine, iminodiacetic acid, nitrilotriacetic acid, ethylenediaminetetraacetic acid, ethylene glycol bis(β-aminoethyl ether)-N,N,N',N'-tetraacetic acid and salts thereof is added, or the above at least one compound is added in combination with boric acid or a salt thereof.

\* \* \* \* \*